United States Patent [19]

Bouheraoua et al.

[11] Patent Number: 5,115,681
[45] Date of Patent: May 26, 1992

[54] ACOUSTIC METHOD AND DEVICE FOR LOCALIZATION OF DEFECTS IN MATERIAL

[75] Inventors: Ahmed Bouheraoua, Breuillet; Bernard Lechelle, Garches, both of France

[73] Assignee: Avions Marcel Dassault-Breguet Aviation, Vaucresson, France

[21] Appl. No.: 513,220

[22] Filed: Apr. 23, 1990

[30] Foreign Application Priority Data

Apr. 24, 1989 [FR] France ................. 89 05410

[51] Int. Cl.$^5$ ............................................. G01N 29/14
[52] U.S. Cl. .................................... 73/801; 73/643
[58] Field of Search .............. 73/587, 801; 367/127; 364/507

[56] References Cited

U.S. PATENT DOCUMENTS

| | | | |
|---|---|---|---|
| 4,033,179 | 7/1977 | Romrell | 73/587 |
| 4,352,167 | 9/1982 | Hashimoto et al. | 367/127 |
| 4,354,388 | 10/1982 | Diepers et al. | |
| 4,586,378 | 5/1986 | Izumi et al. | 73/572 |
| 4,641,526 | 2/1987 | Izumi et al. | 73/587 |
| 4,742,713 | 5/1988 | Abe et al. | |
| 4,979,124 | 12/1990 | Sachse et al. | 73/587 |

FOREIGN PATENT DOCUMENTS 0021196 1/1981 European Pat. Off. .
61-50064 3/1986 Japan .

*Primary Examiner*—John E. Chapman
*Attorney, Agent, or Firm*—Stevens, Davis, Miller & Mosher

[57] ABSTRACT

The method according to the invention consists, in a first step, in studying the acoustic response of a piece P by recording, with acoustic sensors (1, 2, 3, 4), signals emitted by a calibrated acoustic emitter (5), from a succession of predetermined mark points defining a grid on the surface of the piece, while the latter is unstressed. In a second step, the piece is stressed and the acoustic signals coming from acoustic events created by this stressing of the piece are recorded. Processing of the propagation times and of the amplitudes of the acoustic waves thus recorded during these two steps allows identification of the position and size of structural defects in the material constituting the piece P.

12 Claims, 1 Drawing Sheet

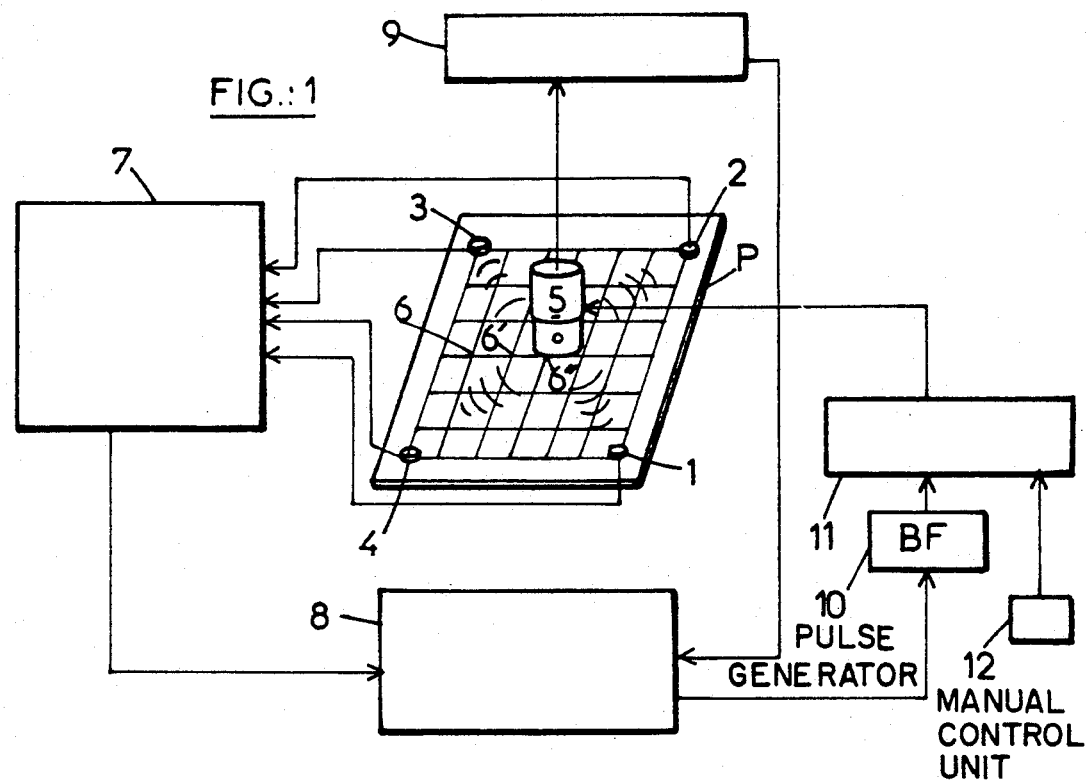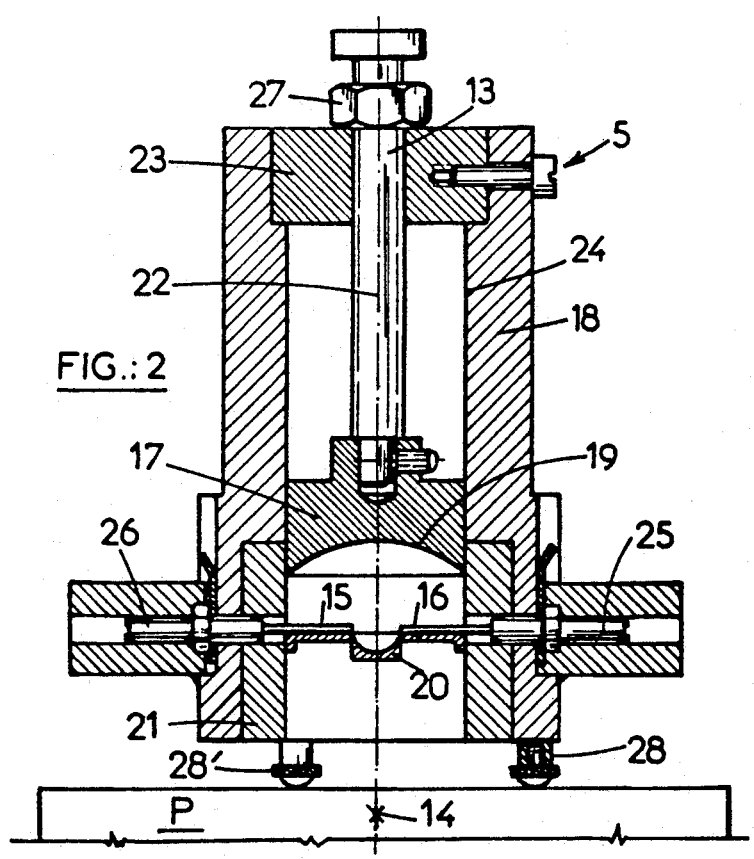

ACOUSTIC METHOD AND DEVICE FOR LOCALIZATION OF DEFECTS IN MATERIAL

The present invention relates to an acoustic method and device for localization of defects in the material constituting a piece and, more particularly but not exclusively, to such a method and such a device designed for the nondestructive testing of pieces made from non-homogeneous materials such as composite materials for example.

A method of nondestructive testing of mechanical pieces is known, which consists in placing the piece under stress and simultaneously auscultating the piece with the aid of acoustic sensors. It is then noted that these sensors record noises which originate in local disorganizations of the material under the stresses applied to the piece, such as, for example, slippage or rupture of fibers in the composite materials, these noises more particularly being created in those places where the substance already presents discontinuities, voids, tears, cracks, and so forth, constituting so many material defects capable of affecting the mechanical strength of the piece. It is thus expedient to localize these defects, in particular when testing pieces for which a high reliability as regards mechanical strength is demanded, as is particularly the case for aircraft structural elements.

According to a first known method, several acoustic sensors are used, arranged around a surface of a thin piece to be auscultated, the propagation times up to the sensors of acoustic signals emitted at the defect points in the stressed piece are measured, and the position of these defect points are referenced by triangulation on the surface of the piece. The position of the defects on the piece can thus be visualized by display on a video screen.

This method is indeed expedient for thin pieces of homogeneous materials where the sound speed is the same in all directions. For pieces from non-homogeneous materials, such as composite materials with fibers arranged in crossed ply and embedded in a synthetic resin for example, it is no longer possible to make this assumption and to accurately localize defects by measurements of propagation times of acoustic signals alone.

Furthermore, according to the known method, an initial adjustment of the response of the piece to acoustic stimulations produced at chosen points on the surface of this piece is carried out, by creating these stimulations with the aid of a simple pencil lead which is broken by being pressed against each of the chosen points. The amplitude and the waveform of the acoustic signal thus injected into the piece cannot be accurately controlled and it is necessary to repeat the operations at each point several times to obtain, by averaging effect, crudely normed measurements. The repetition of measurements requires a great deal of time.

Despite this precaution, for want of the use of an acoustic source with a well-referenced amplitude, it is impossible to exploit the amplitude of the acoustic signals received by the sensors to reconstruct the amplitude of the acoustic wave engendered by the stressing of a defect in the piece. Now, the ability to use the amplitude of the acoustic signal induced by the stressing of a defect in the material would be very fruitful, since this amplitude is very representative of the size of this defect.

The aim of the present invention is therefore to provide an acoustic method and device for localization of defects in a material, in particular in the vicinity of the surface of a piece of this material, which allow accurate localization of the position of the defects detected.

The aim of the present invention is also to provide such a method and such a device allowing measurement of the amplitude of the acoustic waves emitted from these defects during stressing of the piece, in such a way as to allow evaluation of the size of these defects.

The aim of the present invention is further to construct to this end an acoustic emitter able to produce in a repeatable and reproducible way, acoustic waves with calibrated amplitude and wave form, for an injection of these waves at predetermined points of a piece to be studied with the aid of the method according to the invention.

These aims of the invention are attained with an acoustic method for localization of defects in the material constituting a piece, characterized in that, with the aid of at least three noncollinear acoustic sensors arranged on the piece, the propagation times up to these sensors are measured of an acoustic wave injected into the unstressed piece at a succession of mark points distributed over at least part of the surface of the piece, the geometric coordinates of the associated mark points are measured, the propagation times, up to the sensors, of acoustic events triggered by the stressing of the piece are then measured, and with the aid of a norm, applied respectively to the differences between the propagation times measured when unstressed and the propagation times associated with each acoustic event detected in the stressed piece, the coordinates are determined of adjacent mark points which define an element of the surface of the piece covering the part of the latter where an acoustic event induced by the stressing of a structural defect of the material occurs.

According to the invention the position of the defect under the identified surface element is located precisely, through an interpolation of the geometric coordinates of the mark points adjacent to the surface element, weighted by the inverse of a power of the calculated norms relating to these points.

Again according to the invention, as well as the propagation times of the acoustic waves injected into the unstressed piece at the chosen mark points, the amplitudes of the waves received by the sensors are measured, as is also the attenuation of these waves, working from these amplitudes and from those of the injected acoustic wave, the amplitude of an acoustic wave sensed by the sensor in the stressed piece is measured and the original amplitude of this acoustic wave is calculated after localization of the acoustic event which causes it and with the aid of the calculated attenuations of the acoustic waves emitted in the unstressed piece from the mark points localizing this event.

The method according to the invention is implemented with the aid of a device comprising at least three noncollinear acoustic sensors, laid out on the surface of a piece, in order to detect triggered acoustic events, with a view to the localization of possible defects in the material constituting the piece, characterized in that it comprises an emitter of calibrated and reproducible acoustic waves, means of logging the position of a succession of mark points distributed over the surface of the piece, means of stressing the piece, means of acquiring and means of storing the acoustic signals detected by the sensors, on the one hand, in the unstressed piece during emission of acoustic waves successively injected into the piece by the acoustic emitter at each of the mark points, and, on the other hand, in the stressed piece during emission of acoustic waves associated with acoustic events triggered by the stressing of the piece, means of processing the signals stored during the injection of acoustic waves into the unstressed piece and the signals stored following the stressing of the piece, in order to calculate the propagation times, up to the sensors, of the associated acoustic waves and in order to determine, with the aid of a norm applied respectively to the differences between the propagation times measured in the unstressed piece and the propagation times associated with each acoustic event created in the stressed piece, the coordinates of adjacent mark points which define an element of the surface of the piece covering the part of the latter where an acoustic event occurs through the stressing of a defect in the material.

The present invention further provides an acoustic emitter useable in the device described above, this emitter being characterized in that it comprises (a) a reflector of acoustic waves in the form of an ellipsoidal dome, (b) electrodes for forming an electric arc at a focus of the reflector, these electrodes being selectively supplied by a high voltage electricity generator calibrated in such a way that the discharging of an arc between the electrodes is accompanied by the generation of an acoustic pressure wave calibrated in amplitude and in waveform, and (c) a support box for the reflector and for the electrodes, shaped so as to stand on the surface of a piece to be studied in such a way that the acoustic energy emitted at one of the focuses is concentrated, after reflection on the ellipsoidal reflector, at the second focus, thus localized at a point situated below the surface of the piece to be studied.

Other characteristics and advantages of the present invention will emerge from reading the description which follows and on referring to the attached drawing in which:

FIG. 1 is a functional diagram of the acoustic device for localization of defects according to the invention, and FIG. 2 is a view in axial section of an acoustic emitter belonging to the device of FIG. 1.

Reference is made to this figure where the device represented is intended for the localization of structural defects in the material constituting a mechanical piece P which can take various forms.

By way of nonlimiting example, a relatively thin piece has been shown, since it is on such a piece that the position of a structural defect in the material of the piece can most easily be referenced, from the very surface of this piece. The piece P can moreover comprise other elements such as stiffeners (not shown) as is the case for example in airfoils.

In order to localize possible structural defects in the material constituting a part of the piece P, several acoustic sensors 1, 2, 3 and 4 are arranged on the periphery of the surface of the part of the examined piece. Four sensors arranged at the vertices of a rectangle have been shown, but clearly three sensors only could be used to define the studied surface, on condition of course that these sensors are not collinear. Equally, a larger number of sensors could be used at the cost of an increase in the volume of measurements to be processed as will be seen later in the present description, though on the other hand, an increase in the number of sensors is able to allow an increase in the accuracy of the localizations of the defects sought. When an acoustic wave propagates in the piece, starting from a point of the piece situated on or under the surface defined by the acoustic sensors 1, 2, 3 and 4, the propagation times of this wave up to these sensors are a function of the distance separating the point of generation of the acoustic wave from each of the sensors. In the rest of this text, the collection of the propagation times $dt_1$, $dt_2$, $dt_3$, and $dt_4$ of the acoustic wave up to the sensors 1, 2, 3 and 4 respectively, will be given the general name "acoustic image". Thus this "acoustic image" can be associated in a one-to-one manner with the geometric coordinates of the point of emission of the acoustic wave and hence the point of emission can be localized from its acoustic image.

As has been seen above, in a material of inhomogeneous structure such as for example a composite material comprising crossed fiber-ply, embedded in a synthetic resin, by virtue of the structural non-homogeneity and of the anisotropy of the properties of this material, it is not possible to make the assumption according to which the sound propagation speed is uniform in the material.

If the method of the prior art described in the introduction to the present description is then applied to the localization of defects in such a non-homogeneous material, by measurements of propagation times of acoustic waves induced by the stressing of this material and assumed to be propagating with uniform speed, a geographic distribution of the defects in the studied piece will be drawn from these measurements that presents strong distortions due simply to the anisotropy of the sound propagation speed in the material constituting the piece. The present invention allows removal of this, a limitation of the methods of acoustic localization of the prior art.

To achieve this, according to the present invention, in a first step, when the piece is not subjected to any stress, the charting of an "acoustic" mapping of the piece P is carried out. To this end, on the one hand, the "acoustic image" of each of the points of a collection of predetermined mark points defined on the surface of the piece to be explored, and on the other hand, the geometric coordinates of these points are measured and recorded. In order to measure and record the acoustic images of these mark points, according to the invention a novel acoustic emitter 5 is used which will be described more fully later in this text in connection with the study of FIG. 2. The acoustic emitter 5 is successively positioned opposite each of the mark points 6, 6', 6'', etc. defined on the explored surface. It should be noted that these points can be distributed according to a regular or nonregular grid. An irregular grid may be chosen when it is desired to more closely auscultate regions of the piece presenting discontinuities such as, for example, regions neighboring stiffeners, the mechanical behavior of which regions is influenced by the presence of these stiffeners. A great flexibility is available as regards the choice of the distribution of mark points to be used and this distribution can be adapted to pieces of very varied configurations and characteristics.

Having chosen a certain distribution of mark points, the acoustic emitter 5 is successively positioned, as has been seen above, on each of the mark points. At each position, an emission is provoked in the material, opposite this point, of an acoustic wave. As will be seen further on, to this end the emitter 5 comprises two electrodes between which an electric arc is made to flash provoking the formation of an acoustic pressure wave in the material. The acoustic wave thus formed and, according to the invention, perfectly calibrated in amplitude and in waveform for purposes to be revealed further on, propagates in the piece towards the four acoustic sensors 1, 2, 3 and 4. Knowing the instant of emission of the acoustic wave and the instants at which the sensors 1, 2, 3 and 4 successively detect the arrival of this wave, the propagation times $dtloc_{1j}$, $dtloc_{2j}$, $dtloc_{3j}$ and $dtloc_{4j}$ of the wave from the emission point $j$ to each of the four sensors 1, 2, 3 and 4 respectively can be calculated. Thus, four propagation times constituting an acoustic image can be attached to a mark point with index $j$.

According to a variant of this method of establishing the acoustic image of a mark point of the grid, the most recent instant for which the wave reaches one of the four sensors is taken as a reference instant for the measurement of the propagation time. Following this, the subsequent instants at which the wave reaches the three other sensors are logged, and the time intervals which separate these instants from the reference instant are calculated. The acoustic coordinates of the point thus comprise three nonzero components and one zero component, the zero component varying from one mark point to another. Later in this text, these components will be treated as propagation times $dt_i$, although this is not strictly correct.

The signals transmitted by the sensors 1, 2, 3 and 4, which serve in the calculation of these propagation times, are firstly processed by a signal acquisition block 7 which shapes and digitizes these signals in such a way that they can be exploited by processing means 8 consisting of, for example, a computer. Simultaneously with the logging of the signals coming from the sensors, the computer receives, from a block 9, the geometric coordinates (x, y) of the various mark points from which, as has been seen above, acoustic waves suitable for logging the acoustic images of these mark points are emitted. According to a preferred embodiment of the present invention, the signal acquisition block 7 logs not only the instants at which the sensors detect the emitted acoustic wave, but also the amplitude of the wave logged after damping of this wave between the emission point and the sensor under consideration. This measurement, combined with the knowledge of the calibrated amplitude of the emission of the acoustic emitter 5 according to the invention, allows reconstruction of the amplitudes of the acoustic events created in the piece when stressed, these amplitudes allowing evaluation of the size of the defects in the structure of the material which induce these acoustic events.

The acoustic emission of the emitter 5 can be triggered either directly by the computer through a low frequency pulse generator 10 controlling a high voltage generator 11 which supplies the electrodes of the emitter 5, or through a manual control unit 12 of the generator 11. The first solution allows marking of the instant of emission, and measurement of the actual propagation times while initiating a rhythmical emission of electric arcs by the emitter 5, allowing repetition of the measurements in the event of any untoward incident. The second solution relates more particularly to the modified method described above, according to which the propagation times are referenced at the most recent instant at which an acoustic wave reaches one of the four sensors.

Once the set of mark points of the surface has been auscultated with the aid of the acoustic emitter 5, the computer memory contains, for each mark point, its geometric coordinates x, y, its acoustic image consisting of the various measured propagation times or times treated similarly to these propagation times, and the amplitudes of the signals detected by the four sensors, amplitudes which allow determination of the attenuations suffered by the acoustic wave in its propagation between the emitter and each of the four sensors. During the prior measuring phase described above, applied to a piece free from all mechanical stress, the response of the piece to stimulated acoustic events is thereby stored. By virtue of this prior storage, provided by the method according to the invention, the accuracy of the localization of the defects in the piece, once the latter is stressed, is greatly improved as will now be explained.

After this prior measuring phase of the method according to the invention, the piece to be studied is mechanically stressed so that the possible structural defects in the material of which it is made show up through the emission of acoustic waves, or acoustic "events", which are then sensed by the sensors, in terms of instants of arrival and in terms of amplitude, this information then being processed in the computer equipped with suitable software for deducing from it the propagation times $dt_i$ (i varying between 1 and 4 in the case of four sensors) and the attenuations in the signal between the site of the event and the four sensors, with a view to determining the position and the amplitude of the acoustic wave engendered by the event, and hence the size of the defect which causes it.

According to the invention, the piece is progressively stressed, thus provoking the successive appearance of acoustic events which are then distinguished by the instants of appearance in time. The appearance of these acoustic events can be spread out through the choice of a rise in stress presenting phases of increase and judiciously arranged plateaus. Tests have shown that, commonly, an acoustic event is of a few milliseconds duration. To spread out the appearance of these acoustic events in time, a curve of rise in stress could be chosen presenting phases of increase with a duration of 30 seconds to one minute for example, separated by plateaus with a duration of from one to several minutes for example.

The question then arises, for each of the acoustic events successively detected in the piece during the progressive rise in stress of this piece, of determining the position of the defect having induced this acoustic event and the size of this defect, through the amplitude of the detected acoustic event. To do this, use is made of a computer-stored file containing the geometric coordinates and the acoustic images of all the mark points logged during the prior measuring phase, as well as the attenuations of the acoustic wave emitted at each of the mark points, in its propagation towards each of the four sensors of the device.

According to the invention, an approximate position of the defect is first determined, by identifying the four mark points which define the element of the surface of the piece, under which element the defect is localized.

To do this a "norm" is calculated from the propagation times $dt_i$ of the detected acoustic event and from the acoustic images of each of the stored points. In other words, through mathematical operations on the differences in the propagation times measured during the prior measuring phase of the method according to the invention, and measured on perception by the sensors of a specific acoustic event, the four mark points whose distances to the defects are the shortest are determined. The four points define the element of surface covering the detected defect.

A first norm useable to this end is the norm known as "Euclidian" which is expressed in the following form:

$$\sqrt[2]{\sum_{i=1,4} (dtloc_{ij} - dt_i)^2}$$

where $dtloc_{ij}$ denote the propagation times measured during the emission in the unstressed piece of an acoustic wave at a mark point j, and where $dt_i$ denotes the propagation times measured during the acoustic event induced by a defect in the stressed piece, i varying between 1 and 4 in the case of four sensors.

By virtue of a corresponding calculation algorithm programmed in the software executed by the computer, the latter rapidly calculates the four lowest values of this norm, these four lowest values allowing identification of the four mark points defining the element of surface sought.

Other norms could be used to this effect, such as the City block norm:

$$\sum_{i=1,4} \| dtloc_{ij} - dt_i \|$$

the Chebytchev norm:

$$\min_{i=1,4} \| dtloc_{ij} - dt_i \|$$

the norm of order 2:

$$\sqrt[2]{\sum_{i=1,4} ((dtloc_{ij})^2 - (dt_i)^2)^2}$$

the norm of order 3:

$$\sqrt[3]{\sum_{i=1,4} \| dtloc_{ij} - dt_i \|^3}$$

Having thus identified the four points which define the element of surface which covers the defect which it is sought to localize, the position of the defect relative to these four points can be made more precise by interpolations allowing definition of the calculated coordinates x and y of the defect, relative to the surface of the studied piece. The four lowest norm values calculated in the previous phase will be used for this interpolation. Thus, the weighting is carried out by using the inverse of the norm as a weighting coefficient. This weighting favors the nearest points. It has been observed experimentally that in this way, the interpolated points may be somewhat shifted relative to simulated points, chosen close to a mark point. Thus, in order to increase the influence of the near points, a weighting by the inverse of the square of the norm has been chosen. Thus, the following expression:

$$x(n) = \frac{\sum_{n=1,4} x(n) \times \frac{1}{(norm\ n)^2}}{\sum_{n=1,4} \frac{1}{(norm\ n)^2}}$$

where (norm n) represents the norm relative to one of the four mark points n nearest to the defect, and where x(n) corresponds to the x coordinate of each of the four nearest mark points under consideration, allows the x coordinate of the defect to be obtained with a high accuracy, the other geometric coordinate y of the defect, taking an analogous form.

It was observed experimentally that the best results were obtained with an interpolation over four points.

Having thus accurately determined the position of the defect sought, by virtue of the invention it is possible to go further, by evaluating the amplitude of the acoustic wave induced by the presence of the defect during the rise in stress of the studied piece, to then determine the size of the defect which is, as has been seen earlier, strongly related to the amplitude of the emitted acoustic wave.

To do this, the measured attenuations of the acoustic waves emitted during the prior measuring phase, from the mark points which enclose the localized defect, are exploited with the aid of calculation means and suitable software present in the computer. By virtue of the fact that the waves emitted by the acoustic emitter according to the invention are, as will be seen further on, accurately calibrated in amplitude, it is possible, knowing these attenuations, to reconstruct the actual amplitude of the acoustic event created by the defect, on knowing only the amplitude of the wave such as it is when arriving at the sensors employed. To this end, it is possible either to add to the detected amplitude of the wave associated with the event the mean of the attenuations recorded by the four sensors during the emission, in the prior measuring phase, of acoustic waves from the four mark points under consideration, or only to take into account the detected amplitude, at the first sensor reached by the wave, of the wave associated with the event and add to it the mean of the four attenuations above, only in the direction of the first sensor reached.

Once the phase of rise in stress of the piece is completed, and the calculations described above executed by the computer, the latter retains in memory a file of the geometric coordinates of the defects localized and a file of the amplitudes of these defects. It is then possible to visualize, for example by mapping on a video screen, the position of the defects on the piece and/or the size of these defects. The faulty zones of the piece are thus very conveniently visualized and the distribution of the defects as well as their size, can rapidly be assessed. The method according to the invention thus constitutes a powerful means of nondestructive checking of mechanical pieces.

Reference is now made to FIG. 2 in order to describe in detail the structure and the operation of the acoustic emitter which has been created especially to allow the implementation of the invention, in particular in that it allows the visualization of the size of the detected defects through the measurement of the amplitudes of the acoustic waves associated with the acoustic events induced by the presence of these defects during the stressing of the piece studied.

In this figure the acoustic emitter 5 is shown standing on the surface of the piece P to be studied, in such a way that the axis 13 of the emitter is essentially centered on a mark point 14 of the piece 5 where it is desired, in the prior measuring phase, to create an acoustic wave whose propagation in the piece will be followed with the aid of the sensors 1, 2, 3 and 4. Adjustable feet, for example three in number, two of which labelled 28, 28' are visible in the figure, are provided on the emitter with an aim which will be described further on.

The emitter 5 essentially comprises two electrodes 15, 16 separated by an interval centered on the axis 13, and an acoustic reflector 17, the electrodes and the reflector being mounted in a generally cylindrical box 18. The electrodes are supplied by the voltage generator 11 under the control of the computer 8, through the low frequency pulse generator 10 or the manual control box 12 (see FIG. 1). During the discharging of an electric arc between the electrodes 15 and 16, an acoustic pressure wave is produced which is reflected by the reflector 17 and focused in a point 14 inside the piece. This result is attained by giving to a reflective surface 19 of the reflector 17 the form of an ellipsoidal dome centered on the axis 13 meeting the major axis of the ellipsoid, and by positioning the space which separates the electrodes 15 and 16 at the focus of this ellipsoid which is the nearest to this dome. Thus the acoustic waves coming from this focus of the ellipsoid will be reflected by the surface 19 towards the other focus of this ellipsoid, accurately localized at the point 14.

A second acoustic reflector 20 is arranged on the axis 13, presenting a dished reflective surface positioned opposite the surface of the reflector 17. This reflector 20 allows improvement in the concentration of the acoustic waves emitted at the moment of the discharging of the arc between the electrodes 15 and 16. Furthermore, the box 18 is equipped with a lining 21 made of a material which absorbs acoustic waves, which annularly envelopes the space where these waves are engendered, so as to improve the focusing of the acoustic waves at the focus 14, by preventing waves emitted in directions strongly inclined with respect to the axis 13 from adding to those returned by the reflector 17.

It will be further observed in FIG. 2, that the reflector 17 is integral with a screw 22 which passes through an end plug 23 of the emitter 5. The reflector 17 is itself slideably mounted inside a central bore 24 of the box 18 of the emitter and can be displaced inside this bore along the axis 13, by suitable rotation of the screw 22. It is thus possible to accurately set the position of the reflective surface 19 of the reflector 17 in relation to the interval which separates the electrodes 15 and 16, an interval which should preferably be sited at the focus of the ellipsoidal dome which defines this reflective surface 19. The presence of a locking counter-nut 27 on the screw 22 will be further noted, in order to fix, after adjustment, the position of the reflector 17.

A displacement of the focusing point of the acoustic waves, and hence adjustment of the position of this focusing point in relation to the surface of the piece P to be studied can be obtained by suitably setting the height of the adjustable feet.

In order to avoid interference in the environment, and thus possible disturbance in the operation of the items of electronic apparatus which surround the acoustic emitter according to the invention, the box 18 is made of a metallic material which is earthed (grounded), which ensures a shielding in respect of electromagnetic emissions provoked by the discharging of the arcs inside this box. Likewise, the electric power necessary in the production of the arcs is brought to the electrodes 15, 16 by shielded electric cables 25, 26 respectively.

The high voltage generator 11 can conventionally comprise a high voltage transformer. According to a variant (not shown) of the acoustic emitter according to the invention, this generator, connected to the electrodes and to exterior means of electric supply, can be arranged on the acoustic emitter or, better, inside the latter, in order to improve the electrical safety of the device according to the invention.

According to a preferred embodiment of the discharger according to the invention, the two electrodes 15, 16 are a few millimeters apart, and the gap which separates them is arranged about one centimeter above the surface of the piece to be studied.

As has been seen earlier, the acoustic emitter according to the invention is used in a prior measuring phase of the method according to the invention, in order to carry out a recording of the acoustic response of the piece to be studied, from acoustic events provoked at predetermined mark points of the piece. To do this, the emitter is successively placed on the chosen mark points, in order to inject acoustic waves at these points, waves whose propagation in the piece is followed with the aid of the sensors 1, 2, 3 and 4. A spark produced between the electrodes by the generator 11 engenders an acoustic pressure wave. By suitably adjusting the high voltage generator, this pressure wave can be calibrated. This is an important advantage of the emitter according to the invention since, as has been seen earlier, it is by virtue of this calibration of the pressure wave that it is possible to reconstruct, in the phase of recording the acoustic events created in the piece during its stressing, the amplitudes of the acoustic waves associated with these events, in order to thereby allow quantitative evaluation of the size of these events, which is related to that of the defects from which the latter originate. It is thus possible to map the defects in position and to visualize their size.

The present invention thus presents numerous advantages. First of all, by virtue of the novel prior measuring phase of study of the acoustic response of the studied piece, the accuracy in the localization of the defects in the material of the piece is much improved, in particular in the case of pieces made from non-homogeneous materials such as composite materials, presenting a large anisotropy in sound propagation speed. The prior art presented by way of introduction to the present description, limited by the assumption of a uniform propagation speed, introduces large distortions into the acoustic image of such pieces, distortions which unfavorably influence the geometric localization of the defects. The accuracy of the method of localization according to the invention can be further increased by the implementation of the interpolation method described earlier. Furthermore, by virtue of the novel calibrated acoustic emitter used in the invention, a visualization of the size of the defects, impossible in the prior art, is now available.

We claim:

1. Device for localizing defects in a piece of material comprising at least three non-collinear acoustic sensors positioned on the piece, in order to detect acoustic events triggered in the piece, with a view to the localization of possible defects in the material of the piece, said device comprising an emitter of calibrated and reproducible acoustic waves,
   means for logging the position of a succession of mark points distributed over the surface of the piece,
   means for stressing the piece,
   means for acquiring and means for storing the acoustic signals detected by the sensors, on the one hand, in the unstressed piece during emission of acoustic waves successively injected into the piece by the acoustic emitter at each of the mark points, and, on the other hand, in the stressed piece during emission of acoustic waves associated with acoustic events triggered by the stressing of the piece, means for processing the signals stored during the injection of acoustic waves into the unstressed piece and the signals stored following the stressing of the piece, in order to calculate the propagation times to the sensors of the associated acoustic waves and in order to determine, with the aid of a norm applied respectively to the differences between the propagation times measured in the unstressed piece and the propagation times associated with each acoustic event created in the stressed piece, the coordinates of adjacent mark points which define an element of the surface of the piece covering the part of the piece where an acoustic event occurs through the stressing of a defect in the material.

2. Device according to claim 1 in which the means of processing comprise means for interpolation of the geometric coordinates of the mark points adjacent to the identified surface element, with weighting by the inverse of a power of the calculated norms relating to these points, for the determination of the geometric position of an acoustic event induced, in the stressed piece, by a structural defect of the material constituting this piece.

3. Device according to claim 1 in which the means of acquisition of the acoustic signals coming from the sensors log, besides the instant of acquisition of these signals by the sensors, the amplitude of the logged signals, the means of processing being designed to work out from these amplitudes, the amplitudes of the acoustic events induced by the stressing of the piece.

4. Device according to claim 3 comprising means for displaying a mapping of the distribution of the acoustic events created in the stressed piece of the amplitude of these acoustic events.

5. Device according to claim 1 in which the means for processing are part of a computer, this computer comprising means for selectively controlling the triggering of the acoustic emitter.

6. Device according to claim 5 further comprising means for manual triggering of the acoustic emitter.

7. An acoustic method for localization of defects in a piece of material comprising the steps of:

a) injecting an acoustic wave into an unstressed piece of material at a succession of mark points distributed over at least part of the surface of the piece, b) measuring the propagation times of the acoustic waves injected at each of said mark points, to at least three noncollinear acoustic sensors arranged on the piece, c) measuring the geometric coordinates of the associated mark points, d) stressing the piece and measuring the propagation times to the sensors of acoustic events triggered by said stressing, e) determining the coordinates of adjacent mark points that define an element of the surface of the piece which covers the part of the piece where an acoustic event induced by the stressing of a structural defect of the material occurs, with the aid of a norm applied respectively to the differences between the propagation times measured when the piece is unstressed and the propagation times associated with each acoustic event created in the stressed piece.

8. The method according to claim 7, comprising the step of locating precisely the position of the defect within the identified surface element through an interpolation of the geometric coordinates of the mark points adjacent to the surface element, said interpolation being weighted by the inverse of a power of the calculated norms relating to these points.

9. The method according to claim 7, including the step of measuring the amplitudes of the waves received by the sensors and the attenuation of these waves, working from these amplitudes and from those of the injected acoustic wave, measuring the amplitude of an acoustic wave sensed by the sensor in the stressed piece and computing the original amplitude of this acoustic wave after localization of the acoustic even which causes it and with the aid of the calculated attenuations of the acoustic waves emitted in the unstressed piece from the mark points localizing this event.

10. The method according to claim 8, including the step of measuring the amplitudes of the waves received by the sensors and the attenuation of these waves, working from these amplitudes and from those of the injected acoustic wave, measuring the amplitude of an acoustic wave sensed by the sensor in the stressed piece and computing the original amplitude of this acoustic wave after localization of the acoustic even which causes it and with the aid of the calculated attenuations of the acoustic waves emitted in the unstressed piece from the mark points localizing this event.

11. The method according to claim 7, including using at least four sensors and comprising the step of measuring the propagation times of an acoustic wave from the instant of first detection of the acoustic wave by one of the four sensors.

12. The method according to claim 7, including calibrating the amplitude and shape the acoustic wave of step (a).

* * * * *